: US 11,344,871 B2
(45) Date of Patent: May 31, 2022

(12) United States Patent
Singh et al.

(54) PROCESS FOR PREPARATION OF ETHYLENE OLIGOMERIZATION CATALYST AND OLIGOMERIZATION THEREOF

(71) Applicant: Indian Oil Corporation Limited, Mumbai (IN)

(72) Inventors: Gurmeet Singh, Haryana (IN); Rashmi Rani, Haryana (IN); Sukhdeep Kaur, Haryana (IN); Dheer Singh, Haryana (IN); Anju Chopra, Haryana (IN); Gurpreet Singh Kapur, Haryana (IN); Sankara Sri Venkata Ramakumar, Haryana (IN)

(73) Assignee: Indian Oil Corporation Limited, Mumbai (IN)

( * ) Notice: Subject to any disclaimer, the term of this patent is extended or adjusted under 35 U.S.C. 154(b) by 0 days.

(21) Appl. No.: 17/117,171

(22) Filed: Dec. 10, 2020

(65) Prior Publication Data

US 2021/0178376 A1 Jun. 17, 2021

(30) Foreign Application Priority Data

Dec. 11, 2019 (IN) .............................. 201921051272

(51) Int. Cl.
*B01J 31/22* (2006.01)
*B01J 31/14* (2006.01)
*B01J 37/04* (2006.01)
*C07C 2/32* (2006.01)

(52) U.S. Cl.
CPC ............. *B01J 31/22* (2013.01); *B01J 31/143* (2013.01); *B01J 37/04* (2013.01); *C07C 2/32* (2013.01); *B01J 2231/20* (2013.01); *B01J 2531/48* (2013.01); *B01J 2540/442* (2013.01); *C07C 2531/22* (2013.01)

(58) Field of Classification Search
None
See application file for complete search history.

(56) References Cited

U.S. PATENT DOCUMENTS

| 4,361,714 | A | 11/1982 | Langer et al. |
| 4,783,573 | A | 11/1988 | Shiraki et al. |
| 4,855,525 | A | 8/1989 | Young et al. |
| 5,260,500 | A | 11/1993 | Shiraki et al. |
| 5,496,783 | A | 3/1996 | Chauvin et al. |
| 8,653,316 | B2 | 2/2014 | Aliyev et al. |
| 9,050,587 | B2 | 6/2015 | Aliyev et al. |

*Primary Examiner* — Yun Qian
(74) *Attorney, Agent, or Firm* — Blank Rome LLP

(57) ABSTRACT

The present invention describes a catalyst composition for use as a catalyst system for an ethylene oligomerization, providing high activity and produce linear oligomer product having broad weight percent distribution i.e. $C_4$ to $C_{16}$. The catalyst composition comprises a zirconium amide compound, an organoaluminum compound and an additive. The present invention also provides a process for preparation of the zirconium amide compound comprising reacting a zirconium component having formula $ZrX_m \cdot nTHF$, wherein X is halogen atom; m is an integer having value equal or less than 4 and n is a number equal or less than 2, and a substituted amide of formula RCONR'R", wherein R, R' and R" are saturated or unsaturated aliphatic $C_1$-$C_{10}$ hydrocarbon or aromatic $C_6$-$C_{14}$ hydrocarbon, in the presence of an organic solvent.

14 Claims, No Drawings

PROCESS FOR PREPARATION OF ETHYLENE OLIGOMERIZATION CATALYST AND OLIGOMERIZATION THEREOF

RELATED APPLICATION

This application claims the benefit of Indian Application No. 201921051272, filed on Dec. 11, 2019. The entire disclosure of this application is hereby incorporated by reference.

FIELD OF THE INVENTION

The present invention relates to a catalyst composition for use as a catalyst system for an ethylene oligomerization, providing high activity and produce linear oligomer product having broad weight percent distribution i.e. $C_4$ to $C_{16}$. The catalyst composition comprises a zirconium amide compound, an organoaluminum compound and an additive. The present invention also provides a process for preparation of the zirconium amide compound comprising reacting a zirconium component having formula $ZrX_m.nTHF$, wherein X is halogen atom; in is an integer having value equal or less than 4 and n is a number equal or less than 2, with a substituted amide of formula. RCONR'R", wherein R, R' and R" are saturated or unsaturated aliphatic $C_1$-$C_{10}$ hydrocarbon or aromatic $C_6$-$C_{14}$ hydrocarbon, in the presence of an organic solvent.

BACKGROUND OF THE INVENTION

Linear alpha-olefins (LAOs) are olefins or alkenes with a terminal double bond at the primary or alpha position. The position of double bond determines the chemical properties and can undergo all reactions of an olefin including addition metathesis, polymerization etc.
Linear alpha-olefins being extremely versatile are used as precursor for detergents, synthetic lubricants, plasticizers, surfactant and polyolefin. Linear alpha olefins are used as comonomer in the production of polyethylene.

Linear alpha-olefins preparation is largely based on the oligomerization of ethylene. Ethylene oligomerization process produces mixture of even carbon numbered olefins having chain length of 4, 6, 8 and so on with terminal double bonds. It is highly desirable to have terminal double bond but internal olefins formation cannot be ruled out. Also, some amount of polymer is present. The key factor in ethylene oligomerization is to get the desired selectivity, purity of alpha-olefins and product distribution therefore catalyst system and process conditions play an important role. Various types of catalyst system to produce linear alpha-olefins are well known in the art.

U.S. Pat. No. 4,361,714 of Exxon describes a catalyst system comprising of zirconium halide with dialkyl zinc and organoaluminum compound. The oligomerization is performed in a medium of hydrocarbon solvent at temperature of about 50° C. to about 200° C. and at pressure of ethylene of 3.5 to 10.5 MPa. However, the main disadvantage of the catalyst is poor solubility in hydrocarbon solvent and production of wax and high molecular weight polyethylene as by-product in large amount which causes severe reactor fouling.

U.S. Pat. No. 4,783,573 of Idemitsu describes the synthesis of linear alpha-olefins with long chain length in presence of a catalyst system based on a zirconium complex using anhydrous zirconium tetrachloride with aluminum sesquichloride and triethyl aluminum in dry benzene solvent. Organic compounds containing heteroatom, such as alkyldisulphides, thioether, thiophene and primary amine is used as moderator & oligomerization is performed at 120° C. and at pressure of 3.5 MPa. Main disadvantage of the process is poor solubility of zirconium tetrachloride in hydrocarbon solvent, high reaction temperature and its relatively low selectivity of light alpha-olefins.

U.S. Pat. No. 4,855,525 of Exxon disclose a binary catalyst system which includes a zirconium alkyl alkanoates of the general formula $(ZrCl_4.CH_3COOR)_2$ and an organoaluminum compound of the formula $R_nAlX_{3-n}$. The main disadvantage of the catalyst is production of undesirable quantity of high molecular weight polyethylene.

U.S. Pat. No. 5,260,500 of Idemitsu describes a zirconium based catalyst system using alcohol as a third component. In the process, the catalyst components are prevented from contaminating into the product to produce high purity alpha-olefin. The main disadvantage of this system is production of polymers and high yield of $C_{20}+$ fraction.

U.S. Pat. No. 5,496,783 discloses a catalyst system obtained by mixing of zirconium compound with an organic compound chosen from ketals and acetals and hydrocarbyl-aluminum halide. This catalyst is evaluated for ethylene oligomerization and shows good selectivity for light alpha-olefins having 4, 6, 8 and 10 carbon atoms respectively. The product distribution is particularly oriented towards the production of 1-butene with selectivity in best example is 43 wt %. Another disadvantage of the catalyst is low activity and formation of polymer traces which eventually accumulate and causes reactor plugging and prevent a long production run.

U.S. Pat. Nos. 8,653,316 and 9,050,587 of SABIC disclose a catalyst comprising zirconium carboxylate of general formula. $ZrCl_{4-m}(R^1COO)_m$ and an organoaluminum compound of formula $R_2nAlX_{3-n}$. The inventive catalyst system is evaluated for ethylene oligomerization in addition of electron donors to get synergistic effect on selectivity of catalyst system and purity of low molecular weight linear alpha-olefins. However, the main disadvantage of catalyst system is high yield of C20+ fraction.

OBJECTIVES OF THE INVENTION

It is the main objective of the present invention to provide a catalyst composition for use as catalyst system for ethylene oligomerization, which can produce linear alpha-olefins with high purity.

It is also an objective of the present invention to provide a method for preparing an oligomerization catalyst system which can produce linear alpha-olefins with high purity.

Further, the object of this invention is producing linear alpha-olefins with high purity.

Further, the object of the invention is producing broad weight percent distribution linear alpha-olefins.

Further, the object of the invention is oligomerizing ethylene without formation of polymer.

SUMMARY OF ITIE INVENTION

Ethylene oligomerization to obtain alpha olefins in high purity is majorly achieved through efficient catalyst system. While the cocatalyst and reaction conditions support the oligomerization, the nature of catalyst predominately determines what is achievable during the oligomerization. Hence a suitable catalyst is highly desirable.

Accordingly, the present invention provides a catalyst composition for use as catalyst system for ethylene oligomerization, said catalyst composition comprising of a zirconium amide compound having a general formula $ZrX_m \cdot n(RCONR'R'')$, wherein X is halogen atom m is an integer having value equal or less than 4; n is a number equal or less than 2; R, R' and R" are saturated or unsaturated aliphatic $C_1$-$C_{10}$ hydrocarbon or aromatic $C_6$-$C_{14}$ hydrocarbon, an organoaluminum compound and an additive.

In one of the features of the present invention, the zirconium amide compound is tetrachlorobis(N,N-diisobutylacetamide)zirconium $(ZrCl_4 \cdot 2\{CH_3CON[CH_2CH(CH_3)_2]_2\})$.

In one of the features of the present invention, the organoaluminum compound is selected from alkylaluminum, trialkenylaluminum, dialkylaluminum halide, alkylaluminum sesquihalide, dialkylaluminum hydride, partially hydrogenated alkylaluminum, aluminoxane, dialkylaluminum alkoxide and mixture thereof, wherein:
(i) the alkylaluminum is trialkylaluminum and selected from triethylaluminum, triisopropylaluminum, triisobutylaluminum, tri-n-butylaluminum, hexylaluminum, and tri-n-octylaluminum;
(ii) the trialkenylaluminum is triisoprenyl aluminum;
(iii) the dialkylaluminum halide is selected from diethylaluminum chloride, dibutylaluminum chloride, diisobutylaluminum chloride and diethyl aluminum bromide;
(iv) the alkylaluminum sesquihalide is selected from ethylaluminum sesquichloride, butylaluminum sesquichloride and ethylaluminum sesquibromide;
(v) the dialkylaluminum hydride is selected from diethylaluminum hydride and dibutylaluminum hydride;
(vi) the partially hydrogenated alkylaluminum is selected from ethylaluminum dihydride and propylaluminum dihydride;
(vii) the aluminoxane is selected from methylaluminoxane, isobutylaluminoxane, tetraethylaluminoxane and tetraisobutylaluminoxane; and
(viii) the dialkylaluminum alkoxide is diethylaluminum ethoxide.

In another feature of the present invention, the mole ratio of aluminum to zirconium is from 5:1 to 100:1.

In yet another feature of the present invention, the additive is selected from the group consisting of hydrogen, ester, ether, amine, anhydride and sulfur compound. In one of the preferred features, the additive is selected from ethyl acetate, ethyl acetoacetate, ethyl benzoate, anisole, tetrahydrofuran, 1,2-dioxane, thiophen and mixture thereof.

In yet another feature of the present invention, the mole ratio of the zirconium compound and the additive is from 1:0.1 to 1:10.

The present invention also provides a process for preparation of the catalyst composition for use as catalyst system for ethylene oligomerization, the process comprising adding a zirconium amide compound with an organoaluminum compound and an additive, and the zirconium amide compound is prepared by reacting a zirconium component with a substituted amide in the presence of an organic solvent, wherein:
the zirconium amide compound is having formula:

$ZrX_m \cdot n(RCONR'R'')$ wherein X is halogen atom; m is an integer having value equal or less than 4; n is a number equal or less than 2; R, R' and R" are saturated or unsaturated aliphatic $C_1$-$C_{10}$ hydrocarbon or aromatic $C_6$-$C_{14}$ hydrocarbon, the zirconium component is having formula:

$ZrX_m \cdot nTHF$ wherein X is halogen atom; m is an integer having value equal or less than 4 and n is a number equal or less than 2, and the substituted amide is having formula:

$RCONR'R''$ wherein R, R' and R" are saturated or unsaturated aliphatic $C_1$-$C_{10}$ hydrocarbon or aromatic $C_6$-$C_{14}$ hydrocarbon.

Present invention also provides a method of preparation of zirconium amide compound, the method comprising reacting a zirconium component having a formula $ZrX_m \cdot nTHF$, wherein X is halogen atom; m is an integer having value equal or less than 4 and n is a number equal or less than 2, with a substituted amide of formula $RCONR'R''$, wherein R, R' and R" are saturated or unsaturated aliphatic $C_1$-$C_{10}$ hydrocarbon or aromatic $C_6$-$C_{14}$ hydrocarbon, in the presence of an organic solvent.

In one of the features, the present invention is related to the process for preparation of the catalyst composition or the method of preparation of zirconium amide, wherein the zirconium component is tetrachlorobis(tetrahydrofuran) zirconium, $ZrCl_4 \cdot 2THF$.

In one of the features, the present invention is related to the process for preparation of the catalyst composition or the method of preparation of zirconium amide, wherein the zirconium amide compound is having formula $ZrX_m \cdot 2RCONR'R''$ where X can be chlorine or bromine; m is an integer having value equal or less than 4.

In one of the features, the present invention is related to the process for preparation of the catalyst composition or the method of preparation of zirconium amide, wherein the substituted amide is prepared by a process comprising contacting an acyl halide, with a solvating agent and a substituted amine to obtain the substituted amide.

In yet another feature, the present invention is related to the process for preparation of the catalyst composition or the method of preparation of zirconium amide, wherein the acyl halide is represented by RCOX where R is selected from H, $C_1$-$C_{20}$ linear or branched alkyl group which can be linked with cyclic ring, $C_6$-$C_{14}$ aryl group, $C_3$-$C_{15}$ cycloalkyl group, $C_1$-$C_{20}$ alkoxy group, may or may not contain heteroatom and X is selected from halide. In one of the preferred features, the acyl halide is acetyl chloride.

In yet another feature, the present invention is related to the process for preparation of the catalyst composition or the method of preparation of zirconium amide, the substituted amine is represented by R'R"NH where R' & R" are $C_1$-$C_{20}$ linear or branched alkyl group which can be linked with cyclic ring, $C_6$-$C_{14}$ aryl group, $C_3$-$C_{15}$ cycloalkyl group, may or may not contain heteroatom and R' & R" can be same or different. In one of the preferred features, the substituted amine is N,N-diisobutylamine.

In one of the features, the present invention is related to the process for preparation of the catalyst composition or the method of preparation of zirconium amide, wherein the substituted amide is N,N-diisobutylacetamide.

In yet another feature, the present invention is related to the process for preparation of the catalyst composition or the method of preparation of zirconium amide, wherein the mole ratio of zirconium component and substituted amide is from 0.1 to 5.

In yet another feature, the present invention is related to the process for preparation of the catalyst composition or the method of preparation of zirconium amide, wherein the reaction is carried out at a temperature in the range of 20° C. to 170° C.

In one of the features of the present invention, the organic solvent is selected from the group consisting of diethyl ether, dichloromethane, tetrahydrofuran, chlorobenzene, toluene, o-chlorotoluene, xylene, chloroform, and cyclohexane.

The present invention also provides a process for the oligomerization of ethylene without formation of polymer, the process comprising contacting ethylene with the catalyst composition in an inert organic solvent under ethylene oligomerization conditions to obtain linear alpha-olefins with high degree of linearity having 90 mole percent or greater within a molecular weight range of oligomer in the range of 4 to 30 carbon atoms.

In one of the features of the present invention, the inert organic solvent is selected from aromatic hydrocarbon solvent, unsubstituted or substituted with halogen; aliphatic paraffin hydrocarbon; alicyclic hydrocarbon compound; halogenated alkane and mixture thereof, wherein:
  (i) the aromatic hydrocarbon solvent is selected from toluene, benzene, xylene, chlorobenzene, dichlorobenzene, and chlorotoluene;
  (ii) the aliphatic paraffin hydrocarbon is selected from pentane, hexane, heptane, octane, nonane, and decane;
  (iii) the alicyclic hydrocarbon compound is selected from cyclohexane, and decahydronaphthalene; and
  (iv) the halogenated alkane is selected from dichloroethane, and dichlorobutane.

DETAILED DESCRIPTION OF THE INVENTION

The present invention describes a catalyst composition for use as catalyst system for ethylene oligomerization, said catalyst composition comprising of a zirconium amide compound having a general formula $ZrX_m \cdot n(RCONR'R'')$, wherein X is halogen atom; m is an integer having value equal or less than 4; n is a number equal or less than 2; R, R' and R'' are saturated or unsaturated aliphatic $C_1$-$C_{10}$ hydrocarbon or aromatic $C_6$-$C_{14}$ hydrocarbon, an organoaluminum compound and, an additive.

The zirconium amide compound along with organoaluminum compound and an additive is used as catalyst system for ethylene oligomerization providing high activity and producing linear oligomer product having broad weight percent distribution i.e., $C_4$ to $C_{16}$.

In one feature of the present invention, zirconium amide compound is prepared by reacting zirconium component having formula $ZrX_m \cdot nTHF$, wherein X is halogen atom; m is an integer having value equal or less than 4 and n is a number equal or less than 2, and substituted amide of formula RCONR'R'', wherein R, R' and R'' are saturated or unsaturated aliphatic $C_1$-$C_{10}$ hydrocarbon or aromatic $C_6$-$C_{14}$ hydrocarbon, in the presence of organic solvent. In an embodiment, the zirconium component is having formula $ZrX_m \cdot nTHF$, where X can be chlorine or bromine; m is an integer having value equal or less than 4 and n is a number equal or less than 2. The most preferred zirconium component is tetrachlorobis(tetrahydrofuran) zirconium, $ZrCl_4 \cdot 2THF$. In an embodiment, substituted amide is of formula RCONR'R'', wherein R, R' and R'' are saturated or unsaturated aliphatic $C_1$-$C_{10}$ hydrocarbon or aromatic $C_6$-$C_{14}$ hydrocarbon.

Accordingly, the present invention also provides a process for preparing a substituted amide, said process comprising contacting the acyl halide, represented by RCOX, with the solvating agent and substituted amine to obtain the substituted amide. In an embodiment, the solvating agent can be aromatic or aliphatic and polar or non polar in nature, examples not limiting to diethyl ether benzene, decane, kerosene, ethyl benzene, chlorobenzene, dichlorobenzene, toluene, o-chlorotoluene, xylene, dichloromethane, chloroform, cyclohexane and the like. In an embodiment, acyl halides represented by RCOX where R is H, $C_1$-$C_{20}$ linear or branched alkyl group which can be linked with cyclic rings, $C_6$-$C_{14}$ aryl groups, $C_3$-$C_{15}$, cycloalkyl groups, $C_1$-$C_{20}$ alkoxy group, may or may not contain heteroatom and X is selected from halides. Mixtures of acyl halides can also be used. In another embodiment, substituted amines represented by R'R''NH where R' & R'' are $C_1$-$C_{20}$ linear or branched alkyl group which can be linked with cyclic rings, $C_6$-$C_{14}$ aryl groups, $C_3$-$C_{15}$ cycloalkyl groups, may or may not contain heteroatom. Mixtures of substituted amines can also be used. R' & R'' can be same or different. In one feature of the present invention, the acyl halide is added to the solvating agent followed by dropwise addition of the substituted amine. During this addition, the temperature is maintained such that the exothermic is not allowed to increase the temperature by 2° C. This step is important as per safety aspect because addition of acyl halide to amine is displacement reaction which is quite exothermic.

The process of preparation of zirconium amide compound is described. In one feature of the present invention, the mole ratio of zirconium component and substituted amide is from about 0.1 to 5, preferably from 0.5 to 2. In another feature, the temperature of reaction is from about 20° C. to about 170° C., preferably from about 50° C. to about 120° C. In another feature, the zirconium amide compound can be used directly or after purification. In yet another feature, the zirconium amide compound is preferably tetrachlorobis(N,N-diisobutylacetamide)zirconium $(ZrCl_4 \cdot 2\{CH_3CON[CH_2CH(CH_3)_2]_2\}$.

In one feature of the present invention, the zirconium amide compound along with organoaluminum compound and an additive is used as catalyst system for ethylene oligomerization providing high activity and producing linear oligomer product having broad weight percent distribution i.e., $C_4$ to $C_{16}$. In yet another feature, organoaluminum compound include, not limiting, alkylaluminums such as trialkylaluminum such as triethylaluminum, triisopropylaluminum, triisobutylaluminum, tri-n-butylaluminum, tri-n-hexylaluminum, tri-n-octylaluminum; trialkenylaluminums such as triisoprenyl aluminum; dialkylaluminum halides such as diethylaluminum chloride, dibutylaluminum chloride, diisobutylaluminum chloride and diethyl aluminum bromide; alkylaluminum sesquihalides such as ethylaluminum sesquichloride, butylaluminum sesquichloride and ethylaluminum sesquibromide; dialkylaluminum hydrides such as diethyl aluminum hydride and dibutylaluminum hydride; partially hydrogenated alkylaluminum such as ethylaluminum dihydride and propylaluminum dihydride and aluminoxane such as methylaluminoxane, isobutyl aluminoxane, tetraethylaluminoxane and tetraisobutylaluminoxane; diethylaluminum ethoxide, preferably diethylaluminum chloride and ethylaluminum sesquichloride. Mixtures of organoaluminum compound can also be used.

The mole ratio of aluminum to zirconium is from about 5:1 to about 100:1, preferably from about 10:1 to about 70:1.

In one feature, the additive is selected from the group consisting of, esters, ethers, amines, anhydrides and sulfur compounds preferably, ethyl acetate, ethyl acetoacetate, ethyl benzoate, anisole, tetrahydrofuran, 1,2-dioxane, thiophen and mixtures thereof.

The mole ratio of zirconium compound and the additive is from 1:0.1 to 1:10.

In yet another feature, the catalyst for the oligomerization of ethylene produces linear alpha-olefins having a high degree of linearity, such as about 90 mole percent or greater within a desirable molecular weight range, i.e., oligomers of 4 to 30 carbon atoms.

In an embodiment, oligomerization of ethylene is conducted preferably in an inert organic solvent. The inert organic solvents include aromatic hydrocarbon solvents, unsubstituted or substituted with halogens, such as toluene, benzene, xylene, chlorobenzene, dichlorobenzene, chlorotoluene and the like, aliphatic paraffin hydrocarbons, such as pentane, hexane, heptane, octane, nonane, decane and the like, alicyclic hydrocarbon compounds, such as cyclohexane, decahydronaphthalene and the like, halogenated alkanes, such as dichloroethane, dichlorobutane and the like. A mixture of solvents may be used.

The catalyst or catalyst composition utilized in this present invention provides a number of advantages such as: the zirconium amide compound is stable compound and is readily prepared.

The compound is readily soluble when taken along the cocatalyst and additive. The catalyst provides high activity and productivity with linear oligomer product formation having broad weight percent distribution i.e. $C_4$ to $C_{16}$. The process for preparing zirconium amide compound uses $ZrCl_4.2THF$ as a starting compound, which is readily available, very cheap and easy to handle. Excess of amides is not required as 2 moles of amide is sufficient to replace 2 moles of THF in $ZrCl_4.2THF$ and synthesize the required catalyst of formula $ZrX_m.2RCONR'R''$. Substituted amides were synthesized using acyl chloride and amines in solvating agent & used without further purification or recrystallization.

EXAMPLES

The following examples are included herein for illustrative purposes only. Those skilled in the art will appreciate that many modifications may be made in the invention without changing the essence of invention.

Preparation of N,N-diisobutylacetamide

In 100 ml round bottom flask, added acetyl chloride (1 mole) in diethyl ether followed by dropwise addition of N,N-diisobutylamine (1.5 moles). The temperature is maintained such that the exotherm is not allowed to increase the temperature by 2° C. The addition is continued for one hour followed by stirring for 1.5 h. After the completion of the reaction and removal of ether layer, the unreacted amine is neutralized using acidified water followed brine. The ether is removed from the layer by evaporation under vacuum followed by drying. Yield ~85%. NMR: 0.92 ppm (12H), 2.20 (4H), 2.38 (2H), 7.23-7.26 (8H)

Preparation of tetrachlorobis(N,N-diisobutylacetamide)zirconium ($ZrCl_4.2\{CH_3CON[CH_2CH(CH_3)_2]_2\}$)

In 100 ml round bottom flask, added $ZrCl_4.2THF$ (1 mole) and N,N-diisobutylacetamide (2 moles) in toluene and refluxed at 110° C. for 6 h. On cooling, white solid precipitates out and is isolated by removing toluene by evaporation under vacuum. The white solid is further dried in vacuo. Yield ~90%. Found (%): C, 41.18; H, 7,44; N, 4.86; Cl, 24,6; Zr, 15.91; C20H42O2N2Cl4Zr. Calculated (%): C, 41.61; H, 7.28; N, 4.85; Cl, 24.62; Zr, 15.80.

Oligomerization of Ethylene using tetrachlorobis(N,N-diisobutylacetamide)zirconium In a charging flask, equipped with nitrogen, 200 ml of dry toluene was added followed by addition of tetrachlorobis (N,N-diisobutylacetamide)zirconium (0.25 mmol). This dark brown mixture was stirred for 15 minutes and dissolution of the catalyst was observed. Then neat EASC (Al/Zr=17.5) was added to the solution followed by addition of ethyl acetate as the additive. At this point complete dissolution of catalyst was observed. This dark brown solution was charged into preconditioned reactor at 30° C. The oligomerization was conducted at 80° C. and 30 bar ethylene pressure for 60 minutes. After the retrieval of clear liquid, it was treated with 10 ml methanol for quenching the catalyst system. There was no wax formation as well as polymer formation and if polymer was detected, it was only in traces.

Ethylene oligomerization using different conditions and details of the conditions is provided in Table 1. The additive used is ethyl acetate (EA). The cocatalyst is ethylene aluminum sesquichloride (EASC).

Abbreviations:
1. EASC=ethylene aluminum sesquichloride
2. DEAC=diethylaluminum chloride
3. EA=ethyl acetate
4. $ZrCl_4.2THF$=tetrachlorobis(tetrahydrofuran) zirconium
5. $ZrCl_4$=Zirconium tetrachloride
6. $Zr((CH_3)_2CHCH_2COO)_4$=Zirconium tetraisobutyrate
7. TEAL=triethyl aluminum chloride
8. TIPA=triisoprenyl aluminum
9. DBAH=dibutylaluminum hydride
10. DEAE=diethylaluminum ethoxide
11. MAO=methylaluminoxane

TABLE 1

| S No. | Al/Zr (mol) | EA (mmol) | Productivity (g LAO/g Zr) | Distribution of α-olefins (wt %) | | | | α-olefins (wt %) |
|---|---|---|---|---|---|---|---|---|
| | | | | C4 | C6-C10 | C12-C18 | C20+ | |
| OLM#40 | 17.5 | 0.125 | 3300 | 37.0 | 55.2 | 7.6 | 0.2 | >96 |
| OLM#41 | | 0.125 | 3400 | 38.7 | 54.8 | 6.4 | 0.1 | >96 |
| OLM#43 | | 0.125 | 3300 | 39.1 | 54.6 | 6.1 | 0.1 | >96 |
| OLM#11 | | 0.0 | 3100 ~40 mg polymer | 33.3 | 60.9 | 5.7 | 0.1 | >95 |
| OLM#10 | | 0.25 | 2800 | 30.0 | 62.4 | 7.5 | 0.1 | >97 |
| OLM#13 | 35 | 0.125 | 2900 | 35.2 | 59.4 | 5.3 | 0.04 | >97 |
| OLM#14 | 25 | 0.125 | 3100 | 40.4 | 55.7 | 3.9 | 0.04 | >96 |

TABLE 1-continued

|  | Al/Zr | EA | Productivity | Distribution of α-olefins (wt %) | | | | α-olefins |
|---|---|---|---|---|---|---|---|---|
| S No. | (mol) | (mmol) | (g LAO/g Zr) | C4 | C6-C10 | C12-C18 | C20+ | (wt %) |
| OLM#15 | 17.5 (DEAC) | 0.125 | 2800 | 38.5 | 57.1 | 4.4 | 0.1 | >98 |
| OLM#16 | 25 (DEAC) | 0.125 | 3600 | 40.2 | 55.6 | 4.2 | 0.03 | >98 |
| OLM#50 | 17.5 (EASC/DEAC = 3/1) | 0.0 | 2800 | 39.9 | 56.3 | 3.7 | 0.1 | >98 |
| OLM#53 | 17.5 (DEAC/EASC = 3/1) | 0.125 | 2800 | 35.5 | 57.7 | 6.7 | 0.2 | >98 |
| Comparative Data | | | | | | | | |
| OLM#56 | 17.5 ZrCl$_4$•2THF as catalyst | 0.125 | 2200 | 32.3 | 58.2 | 9.4 | 0.03 | >90 |
| OLM# | 17.5 Zr((CH$_3$)$_2$CHCH$_2$COO)$_4$ as catalyst | 0.125 | 3400 | 29.9 | 56.8 | 12.8 | 0.5 | ≥95 |
| OLM#07 | 17.5 ZrCl$_4$ as catalyst | 0.125 | 1000 | 15.7 | 70.9 | 13.0 | 0.4 | ≥90 |
| OLM#72 | ZrCl$_4$•CH$_3$COOR$_1$)$_2$. | 0.125 | 2700 | 36.1 | 57.0 | 6.1 | 0.8 | ≥94 |

The above table describes the different attributes of the catalyst system when subjected for oligomerization of ethylene.

As seen from Table 1, the oligomerization experiments according to the examples of the present invention result in comparable activity of the new catalyst with an improved distribution of alpha-olefins (weight percent) with a high amount of C4 to C10. Additionally, the purity of the LAO fractions is significantly improved compared to the results of the comparative examples.

TABLE 2

Working examples of using different types of alkyl aluminums for oligomerization of ethylene

| S No. | Alkyl aluminum | Al/Zr (mol) | EA (mmol) | Productivity (g LAO/g Zr) | Distribution of α-olefins (wt %) | | | | α-olefins (wt %) |
|---|---|---|---|---|---|---|---|---|---|
|  |  |  |  |  | C4 | C6-C10 | C12-C18 | C20+ |  |
| OLM#41 | EASC | 17.5 | 0.125 | 3400 | 38.7 | 54.8 | 6.4 | 0.1 | >96 |
| OLM#15 | DEAC | 17.5 | 0.125 | 2800 | 38.5 | 57.1 | 4.4 | 0.1 | >98 |
| OLM#80 | TEAL | 17.5 | 0.125 | 2400 | 87.5 | 10.2 | 5.3 | — | >97 |
| OLM#81 | TIPA | 17.5 | 0.125 | 1450 | 92.3 | 7.1 | 0.6 | — | >92 |
| OLM#82 | DBAH | 17.5 | 0.125 | 1800 | 68.9 | 29.6 | 1.0 | 0.5 | >95 |
| OLM#83 | DEAE | 17.5 | 0.125 | 2100 | 31.4 | 38.5 | 14.9 | 15.2 | >94 |
| OLM#84 | MAO | 17.5 | 0.125 | 1200 | 61.2 | 30.2 | 8.6 | — | >95 |

TABLE 3

Working examples of using different mol ratios of alkyl aluminums for oligomerization of ethylene

| S No. | Alkyl aluminum | Al/Zr (mol) | EA (mmol) | Productivity (g LAO/g Zr) | Distribution of α-olefins (wt %) | | | | α-olefins (wt %) |
|---|---|---|---|---|---|---|---|---|---|
|  |  |  |  |  | C4 | C6-C10 | C12-C18 | C20+ |  |
| OLM#41 | EASC | 17.5 | 0.125 | 3400 | 38.7 | 54.8 | 6.4 | 0.1 | >96 |
| OLM#13 | EASC | 35 | 0.125 | 2900 | 35.2 | 59.4 | 5.3 | 0.04 | >97 |
| OLM#14 | EASC | 25 | 0.125 | 3100 | 40.4 | 55.7 | 3.9 | 0.04 | >96 |
| OLM#101 | EASC | 5 | 0.125 | 180 | 78.2 | 18.9 | 0.6 | — | >68 |
| OLM#102 | EASC | 100 | 0.125 | 320 | 35.1 | 58.9 | 5.9 | 0.1 | >90 |
| OLM#103 | EASC | 2 | 0.125 | ~100 g polymer No oligomerization | — | — | — | — | — |
| OLM#104 | EASC | 200 | 0.125 | ~120 g polymer | — | — | — | — | — |

TABLE 4

Working examples of using different additives for oligomerization of ethylene using EASC as cocatalyst and additive as 0.125 mmol

| S No. | Al/Zr (mol) | Additive | Productivity (g LAO/g Zr) | Distribution of α-olefins (wt %) | | | | α-olefins (wt %) |
|---|---|---|---|---|---|---|---|---|
| | | | | C4 | C6-C10 | C12-C18 | C20+ | |
| OLM#41 | 17.5 | EA | 3400 | 38.7 | 54.8 | 6.4 | 0.1 | >96 |
| OLM#111 | 17.5 | THF | 3200 | 34.5 | 61.4 | 4.0 | 0.1 | >95 |
| OLM#112 | 17.5 | anisole | 3100 | 26.3 | 47.2 | 26.5 | 0.1 | >92 |
| OLM#113 | 17.5 | isobutylamine | 2000 | 38.2 | 46.3 | 14.5 | 1.0 | >86 |
| OLM#114 | 17.5 | thiophene | 2800 | 47.8 | 50.2 | 2.0 | — | >92 |
| OLM#115 | 17.5 | Acetic anhydride | No oligomerization | — | — | — | — | — |

TABLE 5

Working examples of using different mol ratio of EA for oligomerization of ethylene using EASC as cocatalyst and Al/Zr mol ratio as 17.5

| S No. | EA (mol) | Productivity (g LAO/g Zr) | Distribution of α-olefins (wt %) | | | | α-olefins (wt %) |
|---|---|---|---|---|---|---|---|
| | | | C4 | C6-C10 | C12-C18 | C20+ | |
| OLM#10 | 0.0 | 3100 ~40 mg polymer | 33.3 | 60.9 | 5.7 | 0.1 | >95 |
| OLM#41 | 0.125 | 3400 | 38.7 | 54.8 | 6.4 | 0.1 | >96 |
| OLM#11 | 0.25 | 2800 | 30.0 | 62.4 | 7.5 | 0.1 | >97 |
| OLM#92 | 1 | 3100 | 35.1 | 61.8 | 3.0 | 0.1 | >97 |
| OLM#93 | 5 | 3200 | 33.6 | 62.4 | 6.1 | 0.2 | >95 |
| OLM#94 | 10 | 3000 | 37.2 | 59.2 | 3.9 | 0.1 | >96 |
| OLM#95 | 15 | No oligomerization | — | — | — | — | — |

The invention claimed is:

1. A catalyst composition for use as a catalyst system for ethylene oligomerization, said catalyst composition comprising:
   tetrachlorobis(N,N-diisobutylacetamide)zirconium having the formula of $(ZrCl_4 \cdot 2\{CH_3CON[CH_2CH(CH_3)_2]_2\})$;
   an organoaluminum compound; and
   an additive.

2. The catalyst composition as claimed in claim 1, wherein the organoaluminum compound is selected from an alkylaluminum, a trialkenylaluminum, a dialkylaluminum halide, an alkylaluminum sesquihalide, a dialkylaluminum hydride, a partially hydrogenated alkylaluminum, an aluminoxane, a dialkylaluminum alkoxide and a mixture thereof, wherein:
   (i) the alkylaluminum is a trialkylaluminum and selected from triethylaluminum, triisopropylaluminum, triisobutylaluminum, tri-n-butylaluminum, tri-n-hexylaluminum, and tri-n-octylaluminum;
   (ii) the trialkenylaluminum is triisoprenyl aluminum;
   (iii) the dialkylaluminum halide is selected from diethylaluminum chloride, dibutylaluminum chloride, diisobutylaluminum chloride and diethyl aluminum bromide;
   (iv) the alkylaluminum sesquihalide is selected from ethylaluminum sesquichloride, butylaluminum sesquichloride and ethylaluminum sesquibromide;
   (v) the dialkylaluminum hydride is selected from diethylaluminum hydride and dibutylaluminum hydride;
   (vi) the partially hydrogenated alkylaluminum is selected from ethylaluminum dihydride and propylaluminum dihydride;
   (vii) the aluminoxane is selected from methylaluminoxane, isobutylaluminoxane, tetraethylaluminoxane and tetraisobutylaluminoxane; and
   (viii) the dialkylaluminum alkoxide is diethylaluminum ethoxide.

3. The catalyst composition as claimed in claim 1, wherein a mole ratio of aluminum to zirconium is in a range from 5:1 to 100:1.

4. The catalyst composition as claimed in claim 1, wherein the additive is selected from a group consisting of an ester, an ether, an amine, an anhydride and a sulfur compound.

5. The catalyst composition as claimed in claim 1, wherein the additive is selected from ethyl acetate, ethyl acetoacetate, ethyl benzoate, anisole, tetrahydrofuran, 1,2-dioxane, thiophen and a mixture thereof.

6. The catalyst composition as claimed in claim 1, wherein a mole ratio of the zirconium amide compound and the additive is in a range from 1:0.1 to 1:10.

7. A process for preparation of the catalyst composition for use as a catalyst system for an ethylene oligomerization as claimed in claim 1, the process comprising:
   adding the tetrachlorobis(N,N-diisobutylacetamide)zirconium having the formula of $(ZrCl_4 \cdot 2\{CH_3CON[CH_2CH(CH_3)_2]_2\})$ with an organoaluminum compound and an additive, wherein the tetrachlorobis(N,N-diisobutylacetamide)zirconium is prepared by reacting a zirconium component with a substituted amide in the presence of an organic solvent,
   wherein:
   the zirconium component is having a formula:

$$ZrCl_4 \cdot nTHF$$

wherein n is a number having a value equal to 2, and the substituted amide is having a formula:

$$CH_3CON[CH_2CH(CH_3)_2]_2.$$

8. A method of preparation of the tetrachlorobis(N,N-diisobutylacetamide)zirconium having the formula of $(ZrCl_4 \cdot 2\{CH_3CON[CH_2CH(CH_3)_2]_2\})$ of the catalyst composition for use as a catalyst system for ethylene oligomerization as claimed in claim 1, the method comprising:

reacting a zirconium component having a formula $ZrCl_4 \cdot nTHF$, wherein n is a number having a value equal to 2, with a substituted amide of formula $CH_3CON[CH_2CH(CH_3)_2]_2$, in presence of an organic solvent.

9. The method of preparation of the zirconium amide compound as claimed in claim 8, wherein, the zirconium component is tetrachlorobis(tetrahydrofuran) zirconium, $ZrCl_4 \cdot 2THF$.

10. The method of preparation of the zirconium amide compound as claimed in claim 8, wherein a mole ratio of the zirconium component and the substituted amide is in a range from 0.1 to 5.

11. The method of preparation of the zirconium amide compound as claimed in claim 8, wherein the reaction is carried out at a temperature in a range of 20° C. to 170° C.

12. The method of preparation of the zirconium amide compound as claimed in claim 8, wherein the organic solvent is selected from the group consisting of diethyl ether, dichloromethane, tetrahydrofuran, chlorobenzene, toluene, o-chlorotoluene, xylene, chloroform, and cyclohexane.

13. A process for an oligomerization of ethylene without formation of a polymer, the process comprising:

contacting ethylene with the catalyst composition as claimed in claim 1 in an inert organic solvent under ethylene oligomerization conditions to obtain linear alpha-olefins with a high degree of linearity having 90 mole percent or greater within a molecular weight range of an oligomer having 4 to 30 carbon atoms.

14. The process as claimed in claim 13, wherein the inert organic solvent is selected from an aromatic hydrocarbon solvent, an unsubstituted or a substituted with halogen; an aliphatic paraffin hydrocarbon; an alicyclic hydrocarbon compound; a halogenated alkane and a mixture thereof, wherein:

(i) the aromatic hydrocarbon solvent is selected from toluene, benzene, xylene, chlorobenzene, dichlorobenzene, and chlorotoluene;

(ii) the aliphatic paraffin hydrocarbon is selected from pentane, hexane, heptane, octane, nonane, and decane;

(iii) the alicyclic hydrocarbon compound is selected from cyclohexane, and decahydronaphthalene; and (iv) the halogenated alkane is selected from dichloroethane, and dichlorobutane.

\* \* \* \* \*